(12) United States Patent
Steiner

(10) Patent No.: US 6,555,127 B2
(45) Date of Patent: Apr. 29, 2003

(54) MULTI-SPIKE RELEASE FORMULATION FOR ORAL DRUG DELIVERY

(75) Inventor: Solomon S. Steiner, Mount Kisco, NY (US)

(73) Assignee: Pharmaceutical Discovery Corporation, Elmsford, NY (US)

( * ) Notice: Subject to any disclaimer, the term of this patent is extended or adjusted under 35 U.S.C. 154(b) by 7 days.

(21) Appl. No.: 09/766,394

(22) Filed: Jan. 19, 2001

(65) Prior Publication Data

US 2001/0046472 A1 Nov. 29, 2001

Related U.S. Application Data

(60) Provisional application No. 60/176,853, filed on Jan. 19, 2000.

(51) Int. Cl.[7] .......................... A61K 47/00; A61K 9/20
(52) U.S. Cl. ...................... 424/439; 424/400; 424/441; 424/468; 424/474; 424/490; 424/464; 514/937; 514/944; 514/974
(58) Field of Search ................................ 424/400, 439, 424/441, 451, 457, 458, 463, 474, 464, 489, 490, 46

(56) References Cited

U.S. PATENT DOCUMENTS

| | | | | |
|---|---|---|---|---|
| 4,904,476 A | * | 2/1990 | Mehta et al. ................ | 424/456 |
| 5,002,776 A | * | 3/1991 | Geoghegan et al. ......... | 424/494 |
| 5,178,878 A | | 1/1993 | Wehling et al. | |
| 5,885,616 A | * | 3/1999 | Hsiao et al. ................ | 424/461 |
| 6,322,819 B1 | * | 11/2001 | Burnside et al. ............ | 424/472 |

FOREIGN PATENT DOCUMENTS

| | | |
|---|---|---|
| EP | 0 379 147 A2 | 7/1990 |
| WO | WO 99/03471 A1 | 1/1999 |
| WO | WO 00/25752 A1 | 5/2000 |
| WO | WO 00/35426 A2 | 6/2000 |
| WO | WO 00/59479 A1 | 10/2000 |

OTHER PUBLICATIONS

Kimko, et al., "Pharmacokinetics and clinical effectiveness of methylphenidate," *Clin Pharmacokinetics* 37(6):457–470 (1999).

Ricchi, et al., "Development of a double pulse release methylphenidate HCL formulation," *Proceedings of the Controlled Release Society* 26:945–946 (1999).

* cited by examiner

*Primary Examiner*—James M. Spear
*Assistant Examiner*—Charesse Evans
(74) *Attorney, Agent, or Firm*—Holland & Knight LLP

(57) ABSTRACT

Methylphenidate or other drugs are provided in a formulation for oral administration that releases the drug in two or more pharmacokinetic spikes, by combining different release forms in a single formulation. In a preferred embodiment for methylphenidate, the first pharmacokinetic spike is achieved by the release of taste-masked methylphenidate which is not enterically coated, while a second pharmacokinetic spike is achieved by the release of methylphenidate in a finely divided form from enterically coated pellets or microparticles formulated for rapid release following dissolution of the enteric coating. A critical aspect of the formulation is the inclusion of excipients that create a burst release following the initial rapid release and uptake. The formulation can be administered as a paste, jelly, suspension, or fast dissolving wafer. To manipulate the dose, the formulation can be provided, for example, as a paste packaged in a tube similar to those used to dispense toothpaste.

20 Claims, No Drawings

US 6,555,127 B2

MULTI-SPIKE RELEASE FORMULATION FOR ORAL DRUG DELIVERY

This application claims priority to U.S. Ser. No. 60/176,853 filed Jan. 19, 2000.

BACKGROUND OF THE INVENTION

The present invention is generally in the field of pharmaceutical formulations, and more particularly related to methods and compositions for controlling the pharmacokinetic profile of drugs, such as methylphenidate, which are used in pharmaceutical applications.

Methylphenidate (trade name RITALIN™) is used to treat hyperactivity and attention deficit disorder (ADD) in children. While it is very effective when administered orally, the effects only last for only about three to four hours. It would be desirable to have a dose form that could be administered in the morning and maintain the child throughout the school day. Typical slow release formulations are not suitable because they produce a continuous slow release, approaching a zero order kinetic release profile. Methylphenidate, however, requires a spike or "saw tooth" (i.e. multi-spike) kinetic profile to be effective in the treatment of ADD.

Methylphenidate is currently being used to treat young children who differ widely in their body weight and hence their dose requirement. A desirable formulation would allow for convenient manipulation of dose by the parent. A more accurate dosing regimen could be achieved if it was provided in a formulation that was amenable to apportionment.

Methylphenidate is currently administered in pill form. It is not administered in an aqueous solution since it is so bitter. Young children frequently have difficulty swallowing pills. It would be advantageous to provide methylphenidate in a form that is easily swallowed by children and that masks the unpleasant taste of the drug.

Methylphenidate is known to be abused by individuals who inject it intravenously to achieve a "high". A desirable formulation would be difficult to inject intravenously and hence would reduce the drug's abuse liability.

It is therefore an object of the present invention to provide a composition for the oral administration of methylphenidate or other drugs that require a multi-spike release.

It is another object of the present invention to provide a composition for the oral administration of methylphenidate or other drugs in an easy to swallow, preferably pleasant tasting, dosage form.

It is a further object of the present invention to provide a composition for oral administration of methylphenidate or other drugs in a form in which the dose of the drug is conveniently manipulated, but which preferably reduces the likelihood of abuse of the drug.

SUMMARY OF THE INVENTION

Methylphenidate or other drugs are provided in a formulation for oral administration that releases the drug in two or more pharmacokinetic spikes, by combining different release forms in a single formulation. In a preferred embodiment for methylphenidate, the first pharmacokinetic spike is achieved by the release of taste-masked methylphenidate which is not enterically coated, while a second pharmacokinetic spike is achieved by the release of methylphenidate in a finely divided form from enterically coated pellets or microparticles formulated for rapid release following dissolution of the enteric coating (i.e., delayed release particles). A critical aspect of the formulation is the inclusion of excipients that create a burst release following the initial rapid release and uptake.

The formulation can be administered as a paste, jelly, suspension, or fast dissolving wafer. The drug can be in the form of drug particles, microencapsulated particles, or drug-polymer particles. In one embodiment, both delayed release and the unprotected methylphenidate are thoroughly mixed and suspended in an appropriate medium to form a paste or a gel. Peanut butter or alginate, flavored with raspberry and a sweetener are examples of the many suitable taste masking agents.

To manipulate the dose, the formulation can be provided, for example, as a paste packaged in a tube similar to those used to dispense toothpaste. The paste can be squeezed out of an orifice of a fixed size such that a given length of paste contains a specified dose of methylphenidate, e.g., one inch contains 5 mg of methylphenidate, two inches contain 10 mg of methylphenidate. An alternative approach is to package the paste in a hypodermic syringe-like dispenser that is calibrated for dose. Yet another alternative approach is to package the formulation as a gelatinous solid, for example, a jelly candy bar. The bar can be scored or marked in units of methylphenidate for convenient dosing. Furthermore, the potential for intravenous abuse of the methylphenidate is markedly reduced when in the form of a semi-solid suspension of particles in a fat based substrate, such as in peanut butter, or a suspension of solid particles in a semi-solid gel.

DETAILED DESCRIPTION OF THE INVENTION

Formulations have been developed for oral administration to release drug, particularly methylphenidate, in two or more pharmacokinetic spikes, by combining different release forms into a single formulation, where a critical aspect of the formulation is the inclusion of excipients or formulation of the drug to produce immediate release and uptake of the drug after a period of time, typically between two and eight hours, most preferably three house, following the initial delivery and uptake of drug.

I. The Drug Formulation and Methods of Making Them

A. Drugs to be Delivered

Although essentially any drug suitable for delivery to the gastrointestinal tract can be delivered in the formulation described herein, the preferred drug is one which is beneficially delivered in two or more pharmacokinetic spikes. The preferred drug is methylphenidate (trade name RITALIN™). This drug is available as methylphenidate hydrochlorid in tablets of 5, 10 and 20 mg for oral administration. A sustained release formulation is also available. These are administered in divided dosages two or three times daily. The formulations described herein are administered to achieve the same effective dosages, but require only a single administration daily.

B. Release Formulations

The multi-release formulation consists of at least two components: drug which is taken up immediately, and is typically in the form of drug particles, drug solution or drug suspension, without any enteric or controlled release coatings or capsule, and drug that is formulated for delayed release, typically in the form of a capsule, coating, or microparticulate formulation, which delays release and uptake of the drug for a period of hours, typically between two and eight hours, more preferably about three hours. The formulation also includes a means for rapid release of the second delayed release component.

Drug formulations are well known. These can consist of pure drug, either in solution (for immediate uptake), in dry powder form, or in suspension. For the delayed release component, the drug must be in a capsule, a coated tablet, or microparticulate formulation, where the drug is not released until the capsule, coating or microparticular material is penetrated by hydrolytic and/or enzymatic action. A variety of enteric coatings, protein coatings or films are well known to delay release.

In a preferred embodiment, additional pharmacokinetic spikes are achieved by the release of drug methylphenidate in a finely divided form from enterically coated pellets or microspheres formulated for rapid release following dissolution of the enteric coating. Pellets or microspheres having different types and/or thicknesses of enteric coatings can be combined to yield two, three or more pharmacokinetic spikes.

In a preferred embodiment, the mixture is pelletized into small particles by any one of several methods known to those skilled in the art of pharmaceutics. The pellets are then coated with any one of a number of pH sensitive enteric coating materials, which are water-resistant, by any one of several methods known to those skilled in the art of pharmaceutics.

Rapid release means preferably consist of food or drug grade which react upon exposure to water and/or a defined pH to rapidly generate a burst of gas, for example, carbon dioxide, which "blows apart" the coating, capsule or particulate composition. Typically, these will be a food acid in dry form (such as citric acid) and a dry powder substance that in combination with water and acid will rapidly form and liberate carbon dioxide (such as baking powder).

This step can be done at the same time as the drug is formed into pellets or particles. For example, equal weights of methylphenidate, citric acid and sodium bicarbonate are thoroughly mixed with a binding agent, methylcellulose, pelletized into particles having an average diameter of 2 millimeters and placed in a fluidized bed apparatus for coating with EUDRAGIT™. The pellets will produce the second "spike release" of methylphenidate because the pellets will transit the stomach intact. When the pellets have traveled approximately one third of the length of the small intestines, the pH will have risen sufficiently to dissolve the thin water resistant pH sensitive coating. This takes approximately three to four hours. When water now comes in contact with the citric acid and sodium bicarbonate, a rapid reaction occurs, releasing carbon dioxide and dispersing the methylphenidate, which because it is rapidly dispersed in a finely divided form, will be rapidly absorbed, yielding the second "pharmacokinetic spike".

C. Carriers

The formulation can also contain binders, taste modifying components, food colorings, and viscosity modifying agents. The drug formulation may be in the form of a suspension, capsule, tablet, paste, gel, or solid or semi-solid form such as a "candy bar". The advantages of the suspension, paste, gel, and solid or semi-solid formulations is that they are readily divided into dosages which can be made more exact based on the age and size of the recipient, and are also more difficult to abuse since they are not injectable.

Taste modifying materials are well known. Bubble gum and fruit flavorings are commonly used for pediatric formulations. For example the drug can be dissolved or suspended in an aqueous solution containing sweeteners and/or flavoring agents, which are well known in the art. Peanut butter or alginate, flavored with raspberry and a sweetener are examples of the many mediums suitable as taste masking agents.

Binding agents may also be added if necessary or desirable. For example, the formulation can be administered orally as a paste, jelly, suspension, or fast dissolving wafer. In one embodiment, both the pelletized and the unprotected methylphenidate are thoroughly mixed and suspended in an appropriate medium to form a paste or a gel.

In a preferred embodiment for methylphenidate, the first pharmacokinetic spike is achieved by the release of taste-masked methylphenidate which is not enterically coated, while a second pharmacokinetic spike is achieved by the release of methylphenidate in a finely divided form from enterically coated pellets or microparticles formulated for rapid release following dissolution of the enteric coating.

II. Methods of Administration and Dosage Manipulation

To manipulate the dose, the formulation can be provided, for example, as a paste packaged in a tube similar to those used to dispense toothpaste. The paste can be squeezed out of an orifice of a fixed size such that a given length of paste contains a specified dose of methylphenidate, e.g., one inch contains 5 mg of methylphenidate, two inches contain 10 mg of methylphenidate.

An alternative approach is to package the paste in a hypodermic syringe-like dispenser that is calibrated for dose. Yet another alternative approach is to package the formulation as a gelatinous solid, for example, a jelly candy bar. The bar can be scored or marked in units of methylphenidate for convenient dosing.

Modifications and variations of the present invention will be obvious to those of skill in the art from the foregoing detailed description. Such modifications and variations are intended to come within the scope of the following claims.

I claim:

1. A composition comprising a drug to be orally administered to a patient comprising
   a first component in a form releasing a first dose of the drug immediately following ingestion of the composition; and
   a second component in a form rapidly releasing a second dose of the drug at a second time after release of the first dose,
   wherein the first and second doses provide a multi-splice pharmacokinetic profile of the drug and wherein the rapid release is achieved through the use of reagents that generate a burst of gas upon exposure to water immediately disperse or expose the second dose of the drug so that it can be absorbed through the gastrointestinal tract.

2. The composition of claim 1 wherein the drug is methylphenidate.

3. The composition of claim 1 comprising taste masking materials.

4. The composition of claim 1 wherein the drug of the second component is enteric coated and rapidly released in a finely divided form following dissolution of the enteric coating.

5. The composition of claim 1 wherein the second component is in the form of pellets or microspheres comprising an acid and a dry powder, wherein the dry powder and acid, upon contact with water, will form and liberate carbon dioxide.

6. The composition of claim 5 wherein the acid is a food acid and the dry powder is baking powder.

7. The composition of claim 5 comprising a binding agent wherein the composition is in the form of a solid or semi-solid food or candy.

8. The composition of claim 1 in the form of a paste, jelly, suspension, or fast-dissolving wafer.

9. The composition of claim 1 in the form of a gelatinous solid.

10. A drug dosage dispenser comprising
a composition for the oral administration of a drug to a patient comprising
a first component in a form releasing a first dose of the drug immediately following ingestion of the composition; and
a second component in a form rapidly releasing a second dose of the drug at a second rime after release of the first dose,
wherein the first and second doses provide a multi-spike pharmacokinetic profile of the drug and wherein the rapid release is achieved through the use of reagents that generate a burst of gas upon exposure to water immediately disperse or expose the second dose of the drug so that it can be absorbed through the gastrointestinal tract,
wherein the composition is in the form of a paste or gel, and
a compressible device for dispensing a measured dose of the composition.

11. A method of administering a drug to a patient in need thereof, comprising orally administering a composition that comprises
a first component in a form releasing a first dose of the drug immediately following ingestion of the composition; and
a second component in a form rapidly releasing a second dose of the drug at a second time after release of the first dose,
wherein the first and second doses provide a multi-spike pharmacokinetic profile of the drug and wherein the rapid release is achieved through the use of reagents that generate a burst of gas upon exposure to water to immediately disperse or expose the second dose of the drug so that it can be absorbed through the gastrointestinal tract.

12. The method of claim 11 wherein the drug is methylphenidate.

13. The method of claim 12 wherein the second dose is released after two to eight hours following release of the first dose.

14. The method of claim 11 wherein the composition is in the form of a paste or gel, and is administered using a compressible device for dispensing a measured dose of the composition.

15. The method of claim 11 wherein the composition is in the form of a solid or semi-solid which can be apportioned to provide the correct dosage form, and is apportioned at the time of administration to an individual in need of treatment thereof.

16. The method of claim 11 wherein the second component is in the form of pellets or microspheres comprising an acid and a dry powder, wherein the dry powder and acid, upon contact with water, will form and liberate carbon dioxide.

17. The method of claim 16 wherein the acid is a food acid and the dry powder is baking powder.

18. The method of claim 11 wherein the composition is in the form of a solid or semi-solid food or candy.

19. The method of claim 11 wherein the composition is administered in the form of a paste, jelly, suspension, or fast-dissolving wafer.

20. The method of claim 11 wherein the composition is administered in the form of a gelatinous solid.

* * * * *